(12) United States Patent
Jörgensen

(10) Patent No.: US 8,265,466 B2
(45) Date of Patent: Sep. 11, 2012

(54) COMBINATION AROMA DIFFUSER

(75) Inventor: Carsten Jörgensen, Kastanienbaum (CH)

(73) Assignee: Ming Jen Hsiao, Miaoli County (TW)

( * ) Notice: Subject to any disclaimer, the term of this patent is extended or adjusted under 35 U.S.C. 154(b) by 533 days.

(21) Appl. No.: 12/614,585

(22) Filed: Nov. 9, 2009

(65) Prior Publication Data

US 2011/0108635 A1    May 12, 2011

(51) Int. Cl.
*A61M 16/00* (2006.01)
*F24F 3/14* (2006.01)

(52) U.S. Cl. .................... 392/393; 392/386

(58) Field of Classification Search ........... 392/386–406
See application file for complete search history.

(56) References Cited

U.S. PATENT DOCUMENTS

| | | | | |
|---|---|---|---|---|
| 3,659,604 | A * | 5/1972 | Melville et al. | 128/203.27 |
| 6,289,176 | B1 * | 9/2001 | Martter et al. | 392/392 |
| 6,772,756 | B2 * | 8/2004 | Shayan | 128/203.26 |
| 7,932,482 | B2 * | 4/2011 | Norwood et al. | 219/506 |
| 8,170,405 | B2 * | 5/2012 | Harris | 392/392 |
| 2006/0222347 | A1 * | 10/2006 | Wefler | 392/390 |
| 2007/0058956 | A1 * | 3/2007 | Bankers et al. | 392/386 |
| 2010/0178042 | A1 * | 7/2010 | Neumann et al. | 392/386 |

* cited by examiner

*Primary Examiner* — Thor Campbell
(74) *Attorney, Agent, or Firm* — Ming Chow; Sinorica, LLC

(57) ABSTRACT

A combination aroma diffuser includes a lower housing, a control unit, a display screen, an upper housing, a light-emitting heating unit, a cover member and a speaker. The upper housing and the lower housing admits light so that the displayed digits of the display screen that is kept inside the lower housing are visible when the display screen emits light. The control unit has stored therein music and sounds for output through the speaker. The light-emitting heating unit emits light through the upper housing to heat an aromatic fluid in the cover member into vapor that goes out of air vents of the cover member to the outside open air.

10 Claims, 7 Drawing Sheets

COMBINATION AROMA DIFFUSER

BACKGROUND OF THE INVENTION

1. Field of the Invention

The present invention relates to an aromatic diffuser and more particularly, to a combination aroma diffuser, which provides combined functions of an aroma diffuser, a clock, a music player and a lamp and, which facilitates cleaning of the aromatic fluid container.

2. Description of the Related Art

Many aroma diffusers are commercially available for use to diffuse essential oil into bedroom space, bringing passion, romance and relaxation. However, regular aroma diffusers do not provide any other added functions such as the function of an alarm clock, the function of a lamp or the function of a music player.

Further, a clock or alarm clock displays time with digits or a pointer that gives a metal stress to the user. Further, the sharp ringing sound of an alarm clock makes people to feel uncomfortable.

Further, conventional aroma diffusers commonly use a heat source to heat essential oil into vapor, thereby bringing passion and relaxation. However, the operation of the heat source of a conventional aroma diffuser must be controlled manually by the user. The user cannot control the operation of the heat source automatically at a predetermined time.

Further, the user of an aroma diffuser may regulate a lamp to emit soft light and turns on an audio equipment or music player to play music when using the aroma diffuser to diffuse a pleasant smell. However, the operation of the aroma diffuser, the lamp and the audio equipment or music player must be controlled separately by the user.

It is inconvenient and not economic to use an aroma diffuser, a lamp and an audio equipment or music player for diffusing a pleasant smell and producing sound and lighting effects. Further, conventional aroma diffusers are not highly detachable to facilitate cleaning of the component parts.

Therefore, it is desirable to provide a combination aroma diffuser, which combines an aroma diffuser, a clock (alarm clock) and a music player into a single device and which facilitates cleaning of the component parts.

SUMMARY OF THE INVENTION

The present invention has been accomplished under the circumstances in view. It is main object of the present invention to provide a combination aroma diffuser, which combines the functions of an aroma diffuser, a clock (alarm clock) and a music player, enabling the clock to control the operation of a lamp and a speaker so that a pleasant music is produced when an aromatic fluid is heated by a heat energy from the lamp into vapor to provide a pleasant smell.

It is another object of the present invention to provide a combination aroma diffuser, which automatically turns on a lamp to wake up the user by soft light instead of a sharp ringing sound, or automatically turns off the lamp to tell the user the time to get to bed or to save the energy.

It is still another object of the present invention to provide a combination aroma diffuser, which utilizes a smell to wake up the user gently instead of a sharp ringing sound.

It is still another object of the present invention to provide a combination aroma diffuser, which wakes up the user by means of emitting light to display digits and releasing a pleasant smell and music instead of a sharp ringing sound, avoiding giving any mental stress to the user.

To achieve these and other objects of the present invention, a combination aroma diffuser comprises a light-transmissive lower housing having a bottom wall and an upright peripheral wall, a control unit, which comprises a control circuit board and a control button set operable by a person to control functioning of the control circuit board, a display screen mounted inside the lower housing and electrically connected to the control circuit board to keep the light-emitting display side thereof facing the upright peripheral wall of the lower housing toward the outside for displaying digits by means of emitting light for viewing by a person, a light-transmissive upper housing supported on the topmost edge of the lower housing, a light-emitting heating unit mounted inside the upper housing and electrically connected to the control circuit board and controllable by the control circuit board to emit light and to generate heat when emitting light, and a cover member covered on the top side of the upper housing, the cover member having a fluid chamber defined therein for holding an aromatic substance heatable into vapor by heat generated by the light-emitting heating unit and at least one air vent located on the top side thereof for guiding vapor out of the fluid chamber to the outside open air.

The combination aroma diffuser further comprises a speaker mounted inside the lower housing corresponding to sound holes on the upright peripheral wall of the lower housing and electrically connected to the control circuit board and controllable by the control circuit board to output sounds.

Further, the upper housing and the lower housing can be prepared from transparent or translucent glass, frosted glass, acrylic, plastics, crystal or ceramic in any of a variety of colors or carrying a color design.

Further, the cover member has a plurality of peripheral grooves located on the periphery to facilitate dissipation of heat energy from the inside space of the upper housing during operation of the combination aroma diffuser. Further, the arrangement of the peripheral grooves facilitates removal of the cover member from the upper housing for a cleaning work to clean the fluid chamber.

DETAILED DESCRIPTION OF THE PREFERRED EMBODIMENT

Figure 1:
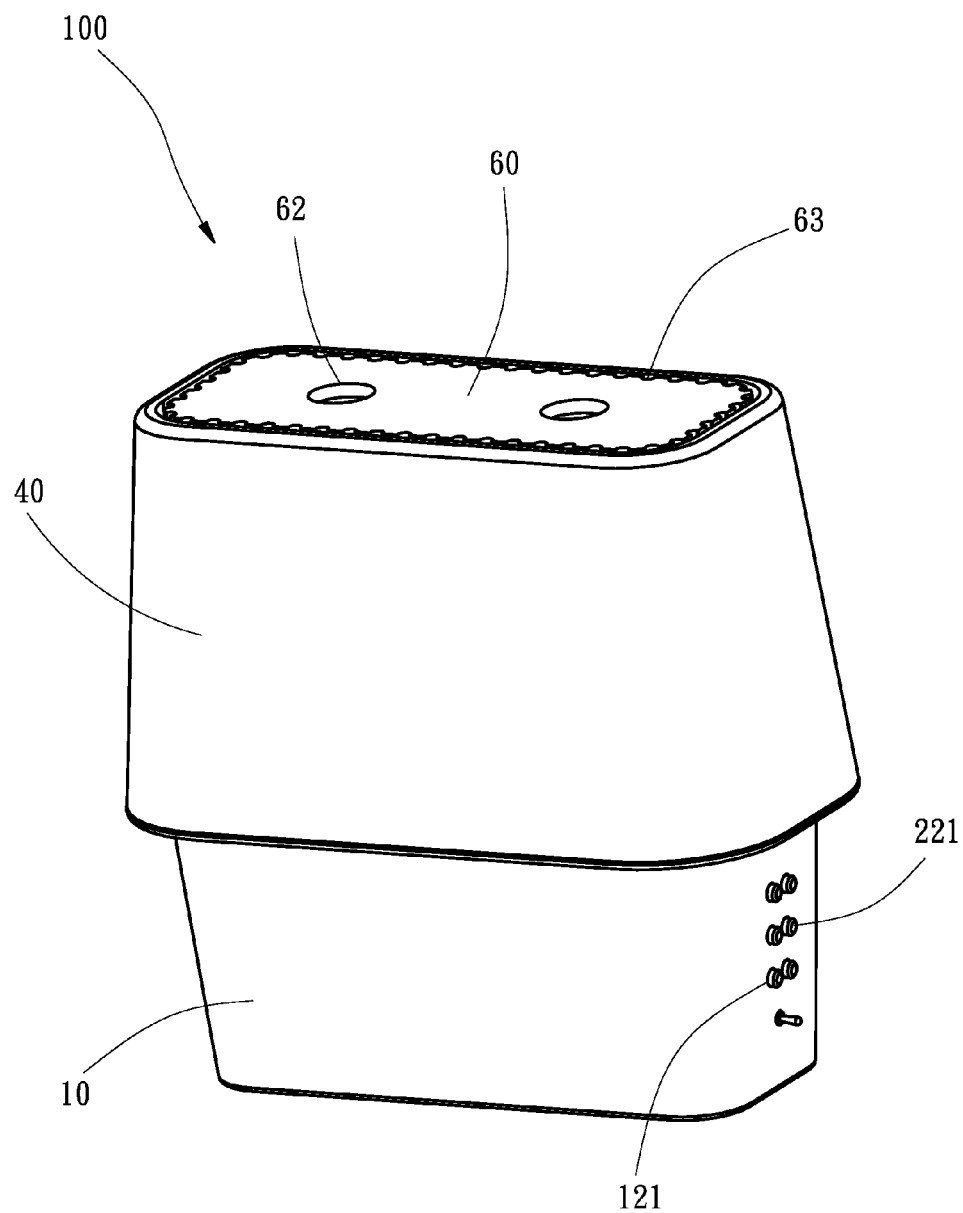
FIG. 1 is an elevational view of a combination aroma diffuser in accordance with the present invention.
Figure 2:
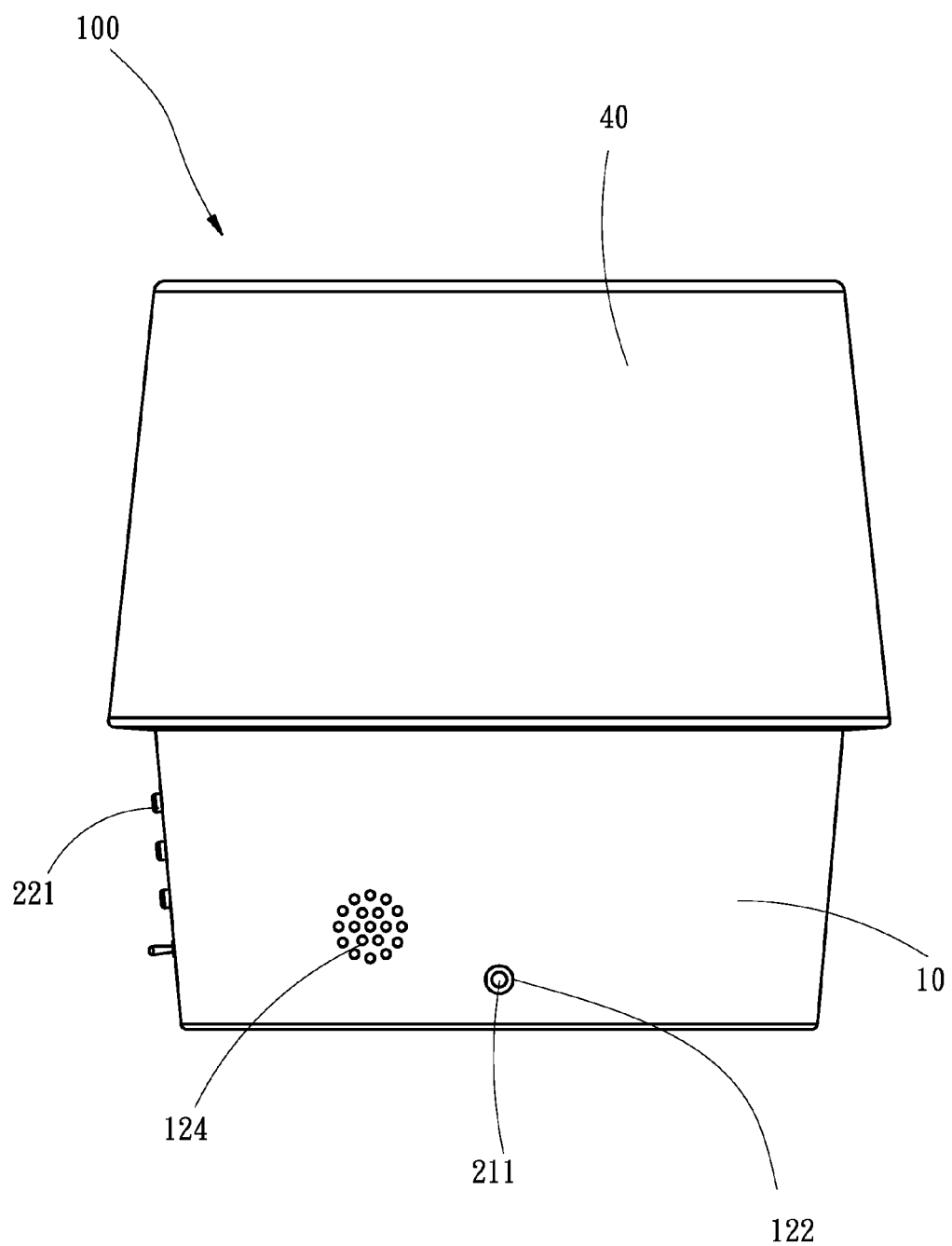
FIG. 2 is a side plain view of the combination aroma diffuser in accordance with the present invention.
Figure 3:
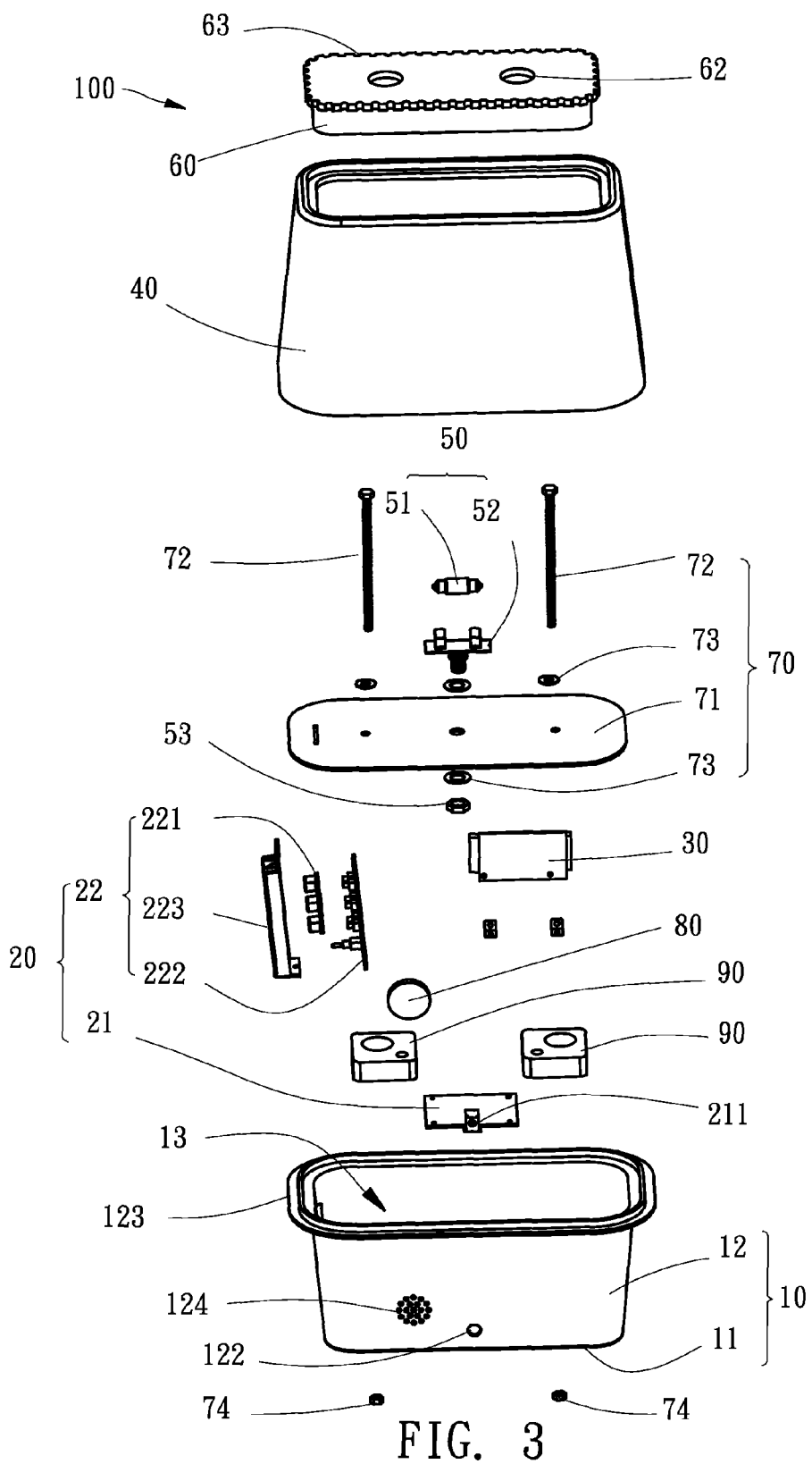
FIG. 3 is an exploded view of the combination aroma diffuser in accordance with the present invention.
Figure 4:
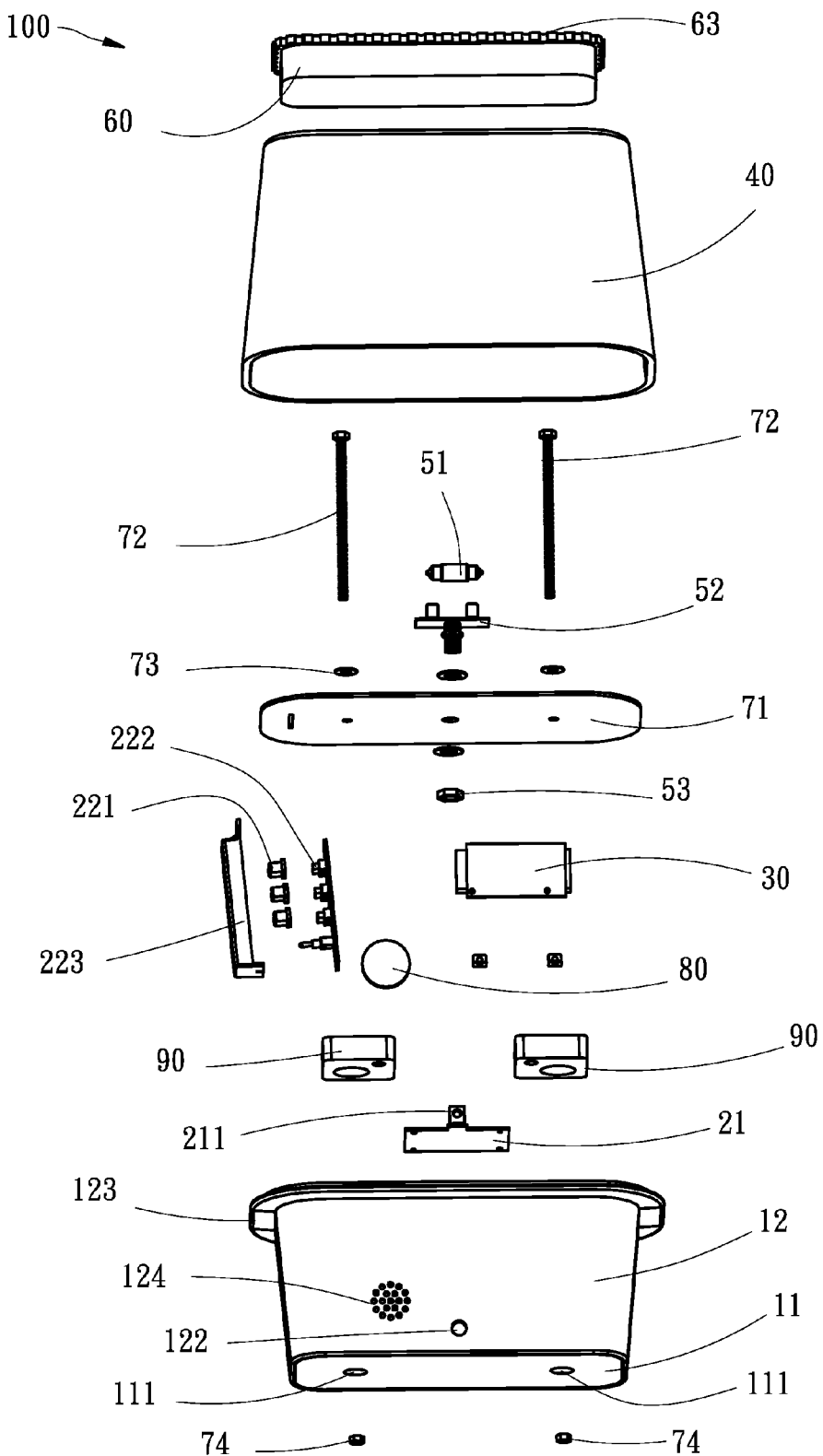
FIG. 4 corresponds to FIG. 3 when viewed from another angle.
Figure 5:
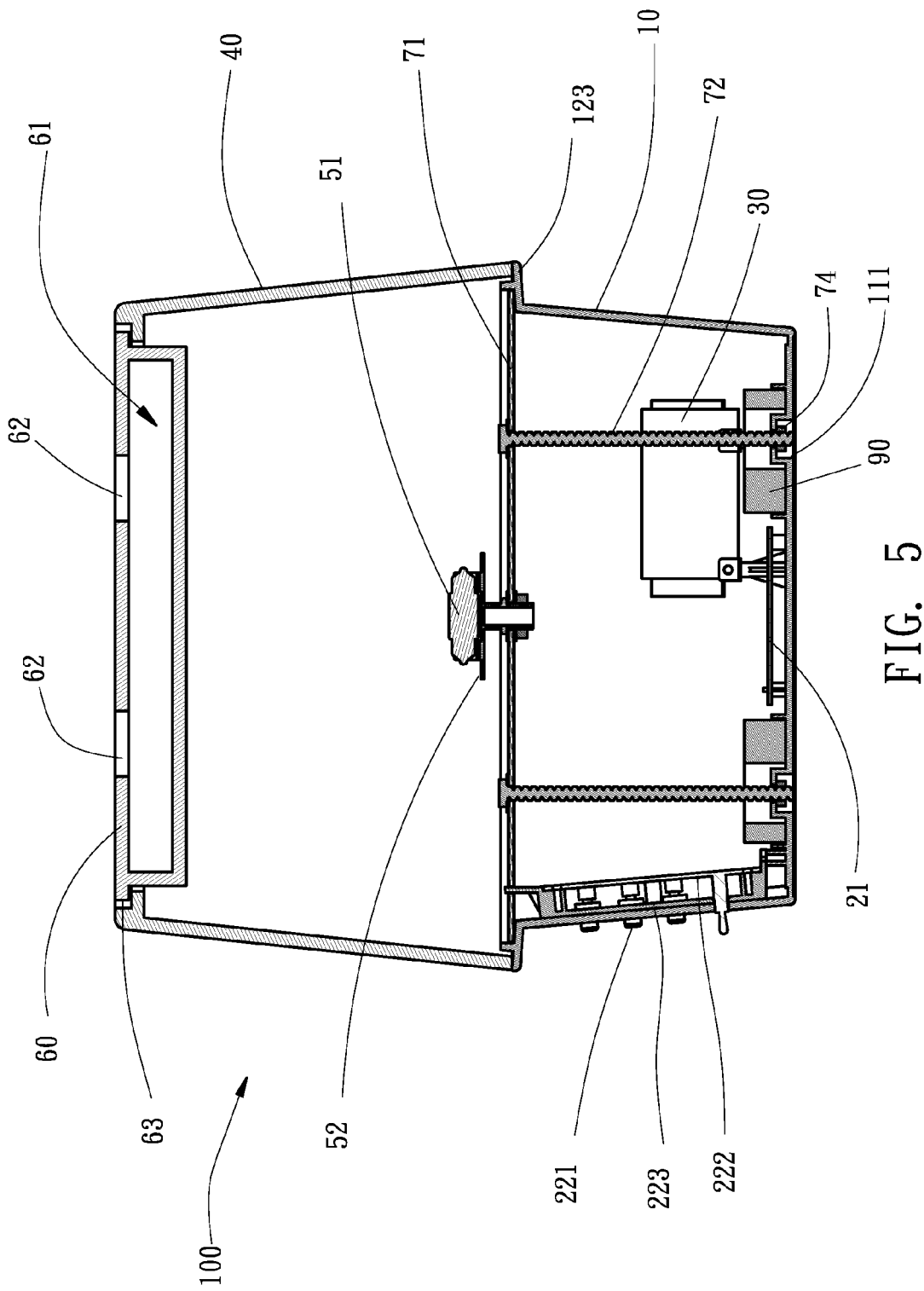
FIG. 5 is a sectional side view of the combination aroma diffuser in accordance with the present invention.
Figure 6:
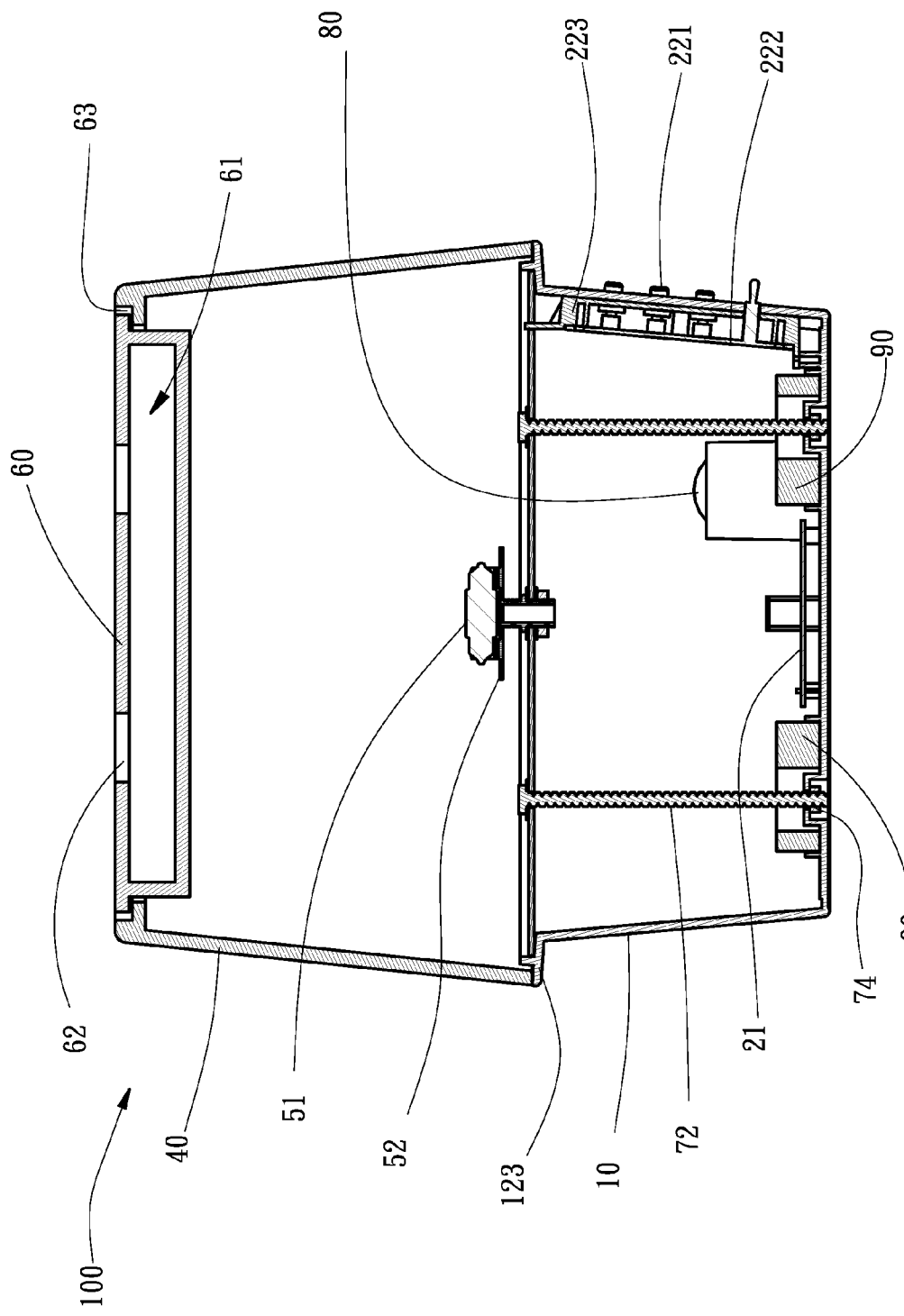
FIG. 6 is another sectional side view of the combination aroma diffuser in accordance with the present invention.

Referring to FIGS. 1 and 2, a combination aroma diffuser 100 in accordance with the present invention is shown comprising a lower housing 10, a control unit 20, a display screen 30, an upper housing 40, a light-emitting heating unit 50 and a cover member 60.

Referring to FIG. 1 and FIGS. 3~6, the lower housing 10 has a bottom wall 11, an upright peripheral wall 12 upwardly extended from the border of the bottom wall 11 and an accommodation chamber 13 surrounded by the bottom wall 11 and the upright peripheral wall 12. The upright peripheral wall 12 has a plurality of button holes 121 and a cable hole 122. The lower housing 10 can be prepared from transparent or translucent glass, frosted glass, acrylic, plastics, crystal or ceramic in any of a variety of colors or carrying a color design.

Referring to FIG. 1 and FIGS. 3~6, the control unit 20 comprises a control circuit board 21 and a control button set 22. The control circuit board 21 is fixedly mounted on the top side of the bottom wall 11 of the lower housing 10, having a power jack 211 aimed at the cable hole 122 for the connection of a power cord (not shown) to provide the necessary working voltage. The control button set 22 includes a plurality of control buttons 221 respectively electrically connected to the control circuit board 21. The control buttons 221 are arranged inside the lower housing 10 and respectively partially extending out of the lower housing 10 through the button holes 121 for pressing by the user to switch on/off power supply, to make a setting or to make a specific control.

Referring to FIGS. 3~6, the display screen 30 is mounted inside the lower housing 10 and electrically connected to the control circuit board 21 for emitting light to display digits, graphics and/or symbols. The light-emitting side of the display screen 30 faces the upright peripheral wall 12 of the lower housing 10 for displaying time, alarm-clock setting time, music playing time or heating time.

Referring to FIGS. 3~6, the upper housing 40 is a hollow open shell having top and bottom open sides. The bottom edge of the upper housing 40 is abutted against the top edge of the lower housing 10. The upper housing 40 can be prepared from transparent or translucent glass, frosted glass, acrylic, plastics, crystal or ceramic in any of a variety of colors or carrying a color design.

Referring to FIGS. 3~6, the light-emitting heating unit 50 is mounted inside the upper housing 40 and controllable to emit light and to generate heat when emitting light.

Referring to FIGS. 1~6, the cover member 60 is a hollow member defining a fluid chamber 61 and a plurality of air vents 62 located on the top wall thereof in air communication with the fluid chamber 61. The cover member 60 is attached to the upper housing 40 to block the top open side of the upper housing 40.

After introduction of the component parts of the combination aroma diffuser 100 and their arrangement, the operational features of the combination aroma diffuser 100 are described hereinafter:

At first, the user can operate the control buttons 221 of the control button set 22 to turn on the light-emitting heating unit 50 or to pre-set the operating time for causing the light-emitting heating unit 50 to operate at a predetermined time period. When the light-emitting heating unit 50 is turned on, it emits light and releases heat to heat an aromatic fluid (essential oil or fragrant wax) carried in the fluid chamber 61 of the cover member 60, causing the aromatic fluid to be changed into aromatic vapor that goes out of the cover member 60 through the air vents 62 into the ambient air to please people. Further, the user can pre-set the operating time of the light-emitting heating unit 50. Subject to settings, the light-emitting heating unit 50 is controlled to emit light through the upper housing 40, simulating the radiation of the rising sun in the morning to wake up the user by light rays instead of a sharp ringing sound. When the light-emitting heating unit 50 is turned off automatically subject to settings, it becomes dark, telling the user the time to get to bed or saving energy.

Further, when the light-emitting heating unit 50 is emitting light, the radiating heat from the light-emitting heating unit 50 heats the aromatic fluid into vapor that carries a smell for waking up the user instead of a sharp ringing sound. Thus, the user can be wakened up comfortably.

Figure 7:
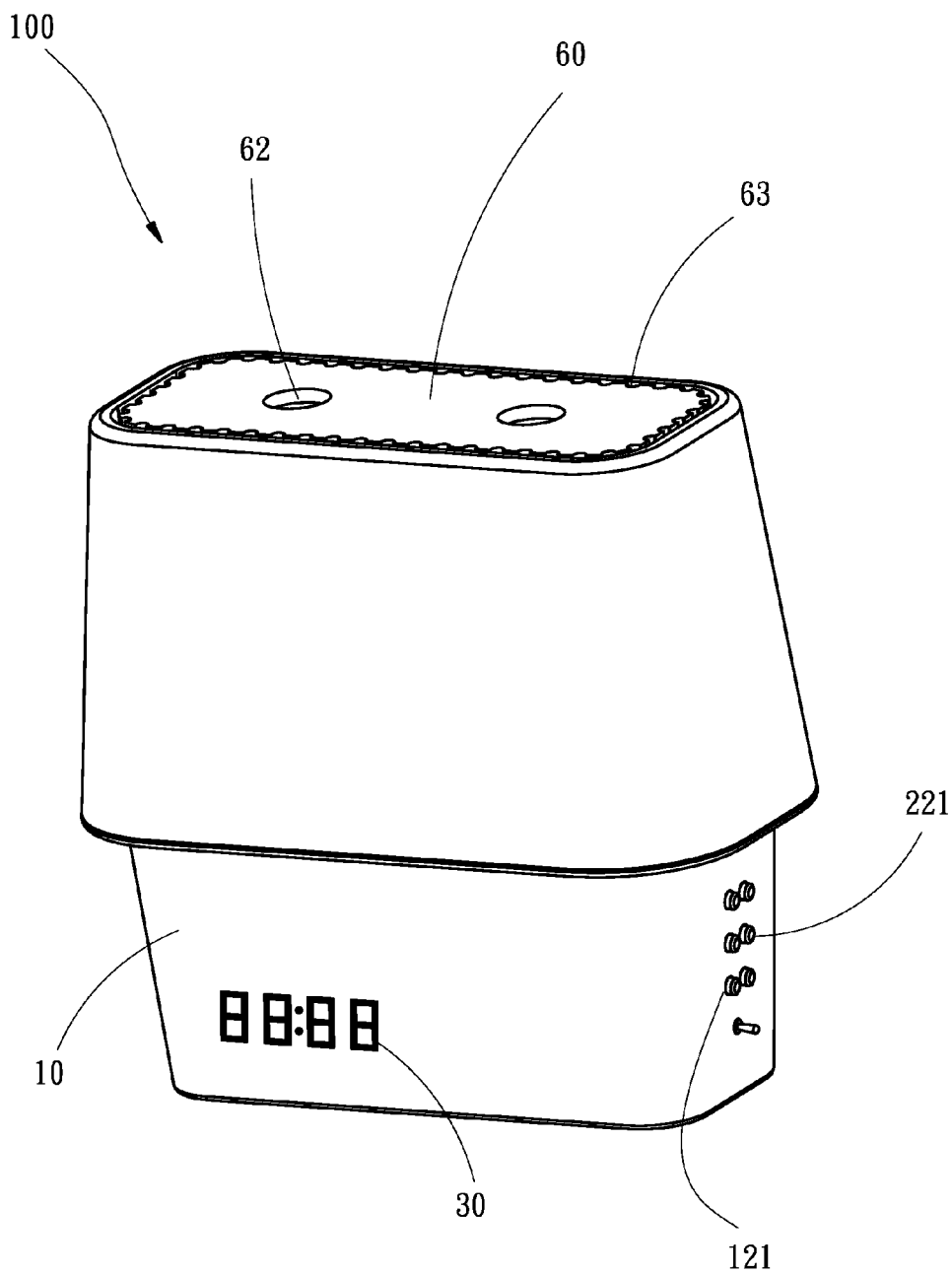
FIG. 7 corresponds to FIG. 1, showing the displayed digits lighted up.

Further, the display screen 30 is concealed inside the lower housing 10. Normally, the displayed digits (time) is not visible. When the pre-set wakeup time is up, light is emitted through the lower housing 10, enabling the user to see the displayed digits (see FIG. 7). Thus, the time variation of the displayed digits will not give any metal stress to the user.

The lower housing 10 further has a rim 123 extended around the top side of the upright peripheral wall 12 for supporting the bottom edge of the upper housing 40 positively and stably.

The lower housing 10 further has two countersunk holes 111 located on the bottom wall 11. The light-emitting heating unit 50 comprises a lamp holder 52 and a lamp 51 detachably mounted on the lamp holder 52.

The combination aroma diffuser 100 further comprises a mounting structure 70 for holding the light-emitting heating unit 50 inside the upper housing 40. The mounting structure 70 comprises a supporting board 71 and two fastening members 72. The supporting board 71 is supported on the rim 123 of the lower housing 10 within the upper housing 40. The lamp holder 52 is locked to the supporting board 71 with a lock nut 53 and an anti-slip washer 73. The two fastening members 72 are screw bolts inserted through the supporting board 71 and fastened to the countersunk holes 111 on the bottom wall 11 of the lower housing 10 with respective nuts 74. Thus, the light-emitting heating unit 50 is firmly secured to the lower housing 10 by the mounting structure 70.

The aforesaid lamp 51 can be, for example, a LED module formed of a red LED chip, a blue LED chip and/or a green LED chip, or a multi-color LED chip.

The aforesaid control button set 22 further includes a circuit board 222 and a bracket 223. The circuit board 222 of the control button set 22 is electrically connected to the control circuit board 21 for enabling the control buttons 221 to act upon the circuit board 22 and to further provide a respective signal to the control circuit board 21. The bracket 223 is adapted for holding the circuit board 222 and the control buttons 221 within the inside wall of the lower housing 10.

The combination aroma diffuser 100 further comprises a speaker 80 mounted inside the lower housing 10 and electrically connected to the control circuit board 21. The upright peripheral wall 12 of the lower housing 10 has sound holes 124 corresponding to the speaker 80 for the passing of output sound waves from the speaker 80. The speaker 80 is adapted for output of natural sounds, music, animal sounds stored in the control circuit board 21 through the sound holes 124, providing a sound effect.

Of course, the user can use the time setting function to control the control circuit board 21 to output storage sounds through the speaker 80 at a predetermined set time for the purpose of morning call instead of a sharp ringing sound.

Further, two weights 90 are affixed to the bottom wall 11 of the lower housing 10 to enhance positioning stability, avoiding falling of the contained aromatic fluid.

The cover member 60 can be prepared from transparent or translucent glass, frosted glass, acrylic, plastics, crystal or ceramic in any of a variety of colors or carrying a color design so that the user can see the volume of the aromatic fluid or fragrant wax contained in the fluid chamber 61 and can give a new supply of the aromatic fluid or fragrant wax before empty, avoiding accident.

Further, the cover member 60 has a plurality of peripheral grooves 63 located on the periphery to facilitate dissipation of heat energy from the inside space of the upper housing 40 during operation of the combination aroma diffuser 100. Further, the arrangement of the peripheral grooves 63 facilitates removal of the cover member 60 from the upper housing 40 for a cleaning work to clean the fluid chamber 61.

As stated above, the combination aroma diffuser has a simple structure and is highly detachable, facilitating cleaning.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A combination aroma diffuser, comprising:
    a lower housing that admits light, said lower housing having a bottom wall and an upright peripheral wall;
    a control unit, said control unit comprising a control circuit board and a control button set operable by a person to control functioning of said control circuit board;
    a display screen mounted inside said lower housing and electrically connected to said control circuit board, said display screen having a light-emitting display side that faces the upright peripheral wall of said lower housing toward the outside for displaying digits by means of emitting light for viewing by a person;
    an upper housing that admits light, said upper housing being supported on the topmost edge of said lower housing;
    a light-emitting heating unit mounted inside said upper housing and electrically connected to said control circuit board and controllable by said control circuit board to emit light and to generate heat when emitting light; and
    a cover member covered on a top side of said upper housing, said cover member having a fluid chamber defined therein for holding an aromatic substance heatable into vapor by heat generated by said light-emitting heating unit and at least one air vent located on a top side thereof for guiding vapor out of said fluid chamber to the outside open air.

2. The combination aroma diffuser as claimed in claim 1, wherein said upright peripheral wall of said lower housing has a plurality of button holes and a cable hole; said control circuit board comprises a power jack aimed at said cable hole for the connection of a power cord; said control button set comprises a plurality of control buttons respectively partially extending out of said lower housing through said button holes.

3. The combination aroma diffuser as claimed in claim 2, wherein said control button set further comprises a circuit board and a bracket, the circuit board of said control button set being electrically connected to said control circuit board for enabling said control buttons to act upon the circuit board of said control button set and to further provide a respective control signal to said control circuit board, said bracket being adapted for holding the circuit board and control buttons of said control button set inside said lower housing.

4. The combination aroma diffuser as claimed in claim 1, wherein said upper housing and said lower housing are prepared from a material selected from a material group of transparent and translucent glass, frosted glass, acrylic, plastics, crystal and ceramic carrying a color design.

5. The combination aroma diffuser as claimed in claim 1, wherein said light-emitting heating unit comprises a lamp holder and a lamp detachably mounted in said lamp holder.

6. The combination aroma diffuser as claimed in claim 5, wherein said lamp is a LED module formed of at least one of a red LED chip, a blue LED chip, a green LED chip and a multi-color LED chip.

7. The combination aroma diffuser as claimed in claim 1, further comprising a mounting structure for holding said light-emitting heating unit inside said upper housing, said mounting structure comprising a supporting board supported on said lower housing within said upper housing to carry said light-emitting heating unit and two fastening members respectively inserted through said supporting board and fastened to the bottom wall of said lower housing to affix said supporting board to said lower housing.

8. The combination aroma diffuser as claimed in claim 1, further comprising a speaker mounted inside said lower housing corresponding to sound holes on the upright peripheral wall of said lower housing and electrically connected to said control circuit board and controllable by said control circuit board to output sounds.

9. The combination aroma diffuser as claimed in claim 1, wherein said cover member is prepared from a material selected from material group of transparent and translucent glass, frosted glass, acrylic, plastics, crystal and ceramic carrying a color design.

10. The combination aroma diffuser as claimed in claim 1, wherein said cover member has a plurality of peripheral grooves for dissipation of heat.

\* \* \* \* \*